United States Patent [19]

Cauquil et al.

[11] Patent Number: 5,220,947
[45] Date of Patent: Jun. 22, 1993

[54] APPARATUS FOR EMPTYING AND RINSING NON-RECOVERABLE FLASKS CONTAINING A TOXIC PRODUCT

[75] Inventors: Gérard Cauquil, Codolet; Henri Chazot, Les Angles, both of France

[73] Assignee: Cogema-Compagnie Generale des Matieres Nucleaires, Velizy Villacoublay, France

[21] Appl. No.: 746,919

[22] Filed: Aug. 19, 1991

[30] Foreign Application Priority Data

Aug. 20, 1990 [FR] France .................... 90 10477

[51] Int. Cl.$^5$ .............................................. G01N 1/00
[52] U.S. Cl. ...................................... 141/91; 141/85; 141/130; 141/285; 141/329; 221/11; 222/400.7; 422/64; 73/863.81
[58] Field of Search ............... 141/85, 89, 91, 130, 141/329, 144–146, 285, 290; 422/64; 222/400.7, 82, 83, 83.5, 88; 73/863.81, 864.12, 864.22, 864.31, 864.35; 221/11, 104, 105

[56] References Cited

U.S. PATENT DOCUMENTS

| 2,562,815 | 7/1951 | Oscroft ................... 141/329 X |
| 2,919,830 | 1/1960 | Anderson ................. 221/11 |
| 3,685,694 | 8/1972 | Ianelli .................... 222/82 |
| 3,764,268 | 10/1973 | Kosowsky et al. ............. 141/130 X |
| 3,765,402 | 10/1973 | Grabhorn ................ 141/329 X |
| 3,993,221 | 11/1976 | Boynton et al. ............. 222/87 |
| 4,094,197 | 6/1978 | Harris, Sr. et al. ............. 73/863.81 |
| 4,192,438 | 3/1980 | Foster et al. ............... 222/5 |
| 4,396,340 | 8/1983 | Clinton ................... 414/412 |
| 4,558,802 | 12/1985 | Molison ................... 221/11 |
| 4,647,432 | 3/1987 | Wakatake ................. 422/64 |
| 4,662,411 | 5/1987 | Zimmermann et al. ............. 141/285 |
| 4,908,320 | 3/1990 | Zakowski et al. ................. 422/64 X |
| 5,012,845 | 5/1991 | Averette ................... 141/329 |
| 5,020,297 | 6/1991 | Borie et al. ................ 141/130 X |

FOREIGN PATENT DOCUMENTS 0249377 12/1987 European Pat. Off. .
1097955 7/1955 France .

Primary Examiner—Charles E. Phillips
Assistant Examiner—Casey Jacyna
Attorney, Agent, or Firm—Pearne, Gordon, McCoy & Granger

[57] ABSTRACT

In order to automatically carry out the emptying and rinsing of non-recoverable bottles or flasks (78) made from a perforatable material such as polyethylene and e.g. containing a low activity solution (88), an apparatus is proposed making it possible to pass the inverted bottles under a double-walled needle (44). The needle (44), operated by a jack, perforates the bottom (82) of the flask (78). Compressed air is then injected into the bottle above the solution (88) through the annular passage formed between the walls of the needle (44), so as to discharge the solution through the central passage of the needle. The flask is then rinsed by injecting pressurized water in place of the compressed air. Finally, the rinsing water is discharged by a further compressed air injection. The emptied and rinsed flasks are then passed to a station, where they are directly discharged into a storage drum.

3 Claims, 3 Drawing Sheets

APPARATUS FOR EMPTYING AND RINSING NON-RECOVERABLE FLASKS CONTAINING A TOXIC PRODUCT

BACKGROUND OF THE INVENTION

1. Field of the Invention

The invention relates to an apparatus making it possible to empty and, if necessary, rinse non-reusable bottles containing a toxic product such as a low activity solution containing gamma emitters and which has been used for carrying out analyses.

2. Description of the Related Art

For analyzing the gamma emitters contained in a low activity solution, frequently a count is made of a certain quantity of liquid introduced before hand into a flask equipped with a cover and sealed by a screw stopper. This flask is conventionally made from a plastics material such as polyethylene. When the analysis is ended the flasks have to be emptied, rinsed and then discharged for storage in drums suitable for receiving waste.

At present, this operation required for each of the flasks the unscrewing of the stopper, the removal of the cover, the emptying of the flask, its rinsing, emptying again and then discharge into a drum. These different operations, which are performed manually within the cell several dozen times every week, are particularly tedious and generally contaminate the work station.

SUMMARY OF THE INVENTION

The present invention relates to an apparatus making it possible to empty and, if necessary, rinse such flasks or bottles in an automated manner and without causing any significant contamination of the work station.

In order to achieve this result, the invention proposes an apparatus for emptying bottles containing a liquid and having at least on perforatable partition, characterized in that it comprises a needle with two coaxial walls, which can be inserted in the bottle through the perforatable partition, the coaxial walls of the needle defining a central passage and an annular passage and means for injecting a pressurized gas into the needle by a first of the said passages, so as to empty the liquid through the other passage.

By perforating the bottom of each of the bottles or flasks with the aid of a double-walled needle and then injecting a gas such as pressurized air into the flask through the needle, it is possible to automatically discharge without any risk of contamination the low activity solutions contained in the flasks.

By also equipping said apparatus with means for injecting a pressurized rinsing liquid through the first passage, it is possible to rinse each of the flasks under the same comfort and safety conditions. After rinsing, the rinsing liquid contained in each flask is discharged by again injecting pressurized gas into each flask through the needle.

Preferably, the first passage by which are injected the pressurized gas and, if appropriate, the pressurized rinsing liquid is the annular passage defined between the coaxial walls of the needle.

Advantageously the needle has an inner tubular wall, an outer tubular wall and a perforating tip or point fixed to at least one of these walls, the outer tubular wall having at least one opening located in an area remote from said perforating tip and the latter has at least one opening issuing into the central passage defined by the inner tubular wall.

In a preferred embodiment of the invention, the apparatus has a rotary barrel able to rotate about a vertical axis and having at least three cavities able to in each case receive an inverted flask, as well as means for rotating the said barrel, so as to successively pass each cavity in front of a loading station, an emptying station having means for moving said needle between an upper waiting position and a lower emptying position, together with a discharge station.

Advantageously, the apparatus according to the invention also has a rotary basket able to rotate about a vertical axis parallel to the drum axis, said basket comprising vertical tubular columns in which can be placed several inverted bottles, a fixed horizontal panel placed below the basket and on which rest the bottles and means for rotating the basket, so as to successively bring each tubular column above an opening formed in the panel, said opening defining the barrel loading station located beneath the said panel.

BRIEF DESCRIPTION OF THE DRAWINGS

A preferred embodiment of the invention is described in greater details hereinafter relative to the attached drawings, wherein show.

DESCRIPTION OF THE PREFERRED EMBODIMENTS

Figure 1:
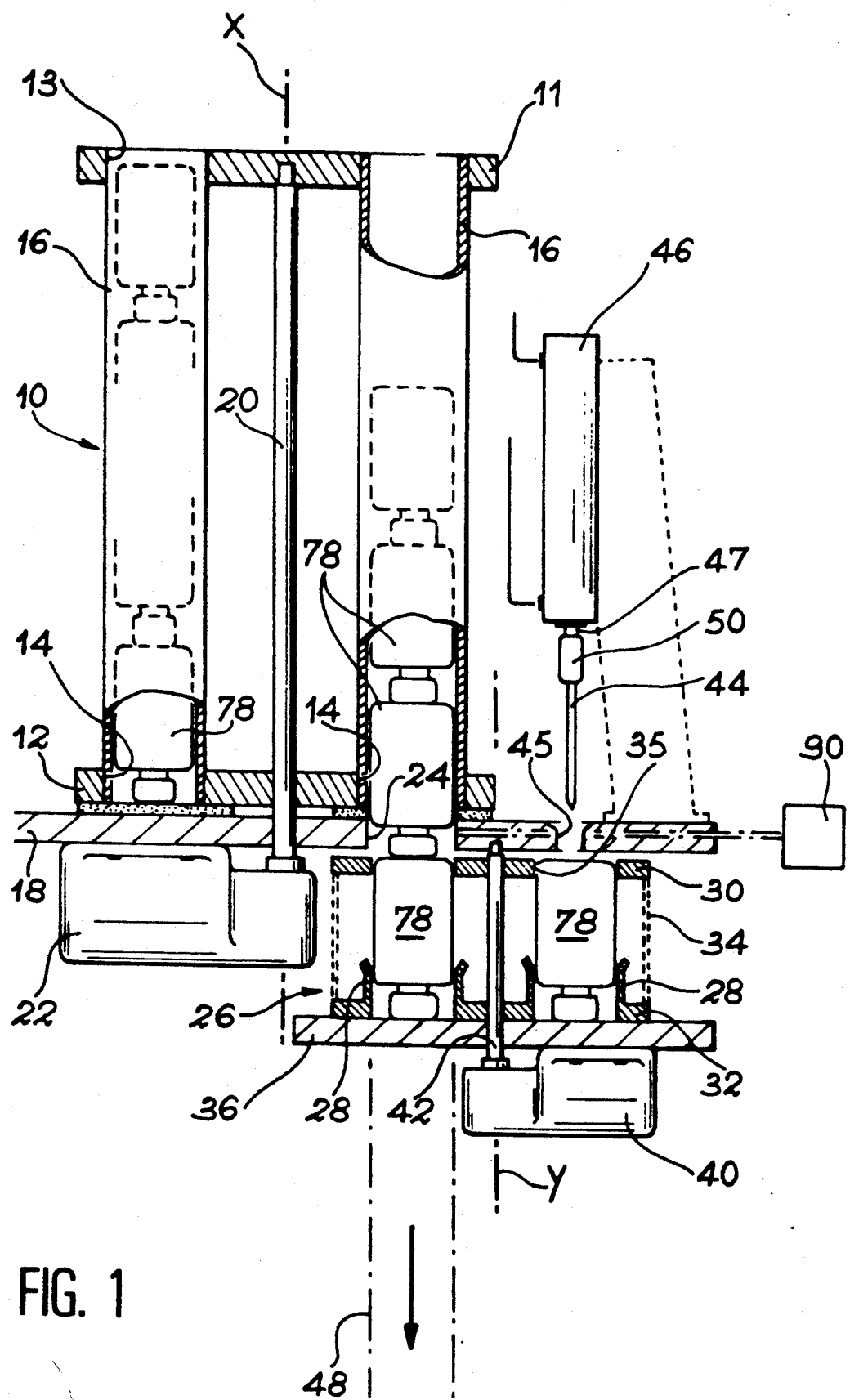
FIG. 1 A front, part sectional view diagrammatically showing a flask emptying and rinsing apparatus according to the invention.

In FIG. 1, the reference numeral 10 designates in general terms a rotary basket having a vertical axis X. This basket 10 comprises a horizontal upper plate 11 and a horizontal lower plate 12 in which are formed respective circular openings 13, 14, e.g. eight such openings, which are regularly distributed around the vertical axis X. The circular openings 13, 14 are linked in pairs by vertically axed, tubular columns 16 fixed to the plates 12.

The rotary basked 10 rests on an upper horizontal panel 18 placed immediately below the plate 12. The plates 11 and 12 are integral with a vertical shaft 20 located along the axis X and which traverses the panel 18. A motor assembly 22 placed below the panel 18 rotates the basket 10 via the shaft 20.

A circular opening 24 having substantially the same diameter as the circular openings 13, 14 is formed in the panel 18 at a location such that each of the circular openings 14 can be successively brought in front of the said circular opening 24 during the rotation of the basket 10.

The emptying and rinsing apparatus illustrated in FIG. 1 also has a rotary drum generally designated by reference numeral 26. This rotary drum has a vertical axis Y displaced with respect to the axis X beyond the axis of the said circular opening 24, in such a way that these three axes are located in the same vertical plane.

The rotary drum 26 is placed below the panel 18 and has three cavities materialized by the vertically axed tubular receptacles 28 regularly distributed around the axis Y. The distance separating each cavity from the axis Y is such that these cavities can be successively brought into the extension of the circular opening 24 by a rotation of the drum 26.

In the embodiment diagrammatically illustrated in FIG. 1, the drum 26 has an upper horizontal plate 30 and a lower horizontal plate 32 interconnected by a peripheral sleeve 34. The lower horizontal plate supports the receptacles 28 and the upper horizontal plate 30 has a circular opening 35 to the right of each of these receptacles.

The drum 26 rests on a lower horizontal panel 36 joined to the upper panel 18, e.g. by not shown small columns. The rotation of the drum 26 around the vertical axis Y is ensured by a motor assembly 40 fitted below the panel 36 and whereof the vertical output shaft 42, positioned along the axis Y, traverses the panel 36 for joining to the plates 30, 32 of the drum 26.

When one of the receptacles 28 of the drum 26 is located in the alignment of the circular opening 24 formed in the panel 18 (said opening constituting the loading station of the drum 26), the two other cavities 28 of the drum 26 respectively face a flask emptying and rinsing station and in front of a flask discharge station. These two latter stations are displaced so as to be located beyond the outer periphery of the basket 10.

The emptying and rinsing station of the flask essentially comprises, according to an essential feature of the invention, a double-walled needle 44, which will be described in greater detail hereinafter relative to FIGS. 2 and 3. This needle 44 is positioned in accordance with a vertical axis substantially aligned with the axis of the receptacle 28 located facing the flask emptying and rinsing station. It is supported by the rod 47 of a needle holder jack 46 permitting its displacement in accordance with its axis between a top waiting position, illustrated in FIG. 1, and a bottom emptying position, illustrated in FIG. 2.

In its top waiting position, the double-walled needle 44 is entirely positioned above the panel 18, whereas where it occupies its bottom emptying position, the needle 44 traverses an opening 45 formed for this purpose in the panel 18 and penetrates the flask received in the corresponding receptacle 28, as will be shown hereinafter.

The discharge station in front of which is located the third cavity 28 of the drum 26 is materialized by a tubular collar 48 placed below a not shown circular opening formed at this point in the panel 36. The flasks are automatically discharged by gravity when they arrive in front of said opening following a rotation of the drum 26. The opposite end of the collar 48 issues directly into a not shown, waste material storage drum, after having passed through the wall of the cell in which the apparatus is located.

Figure 3:
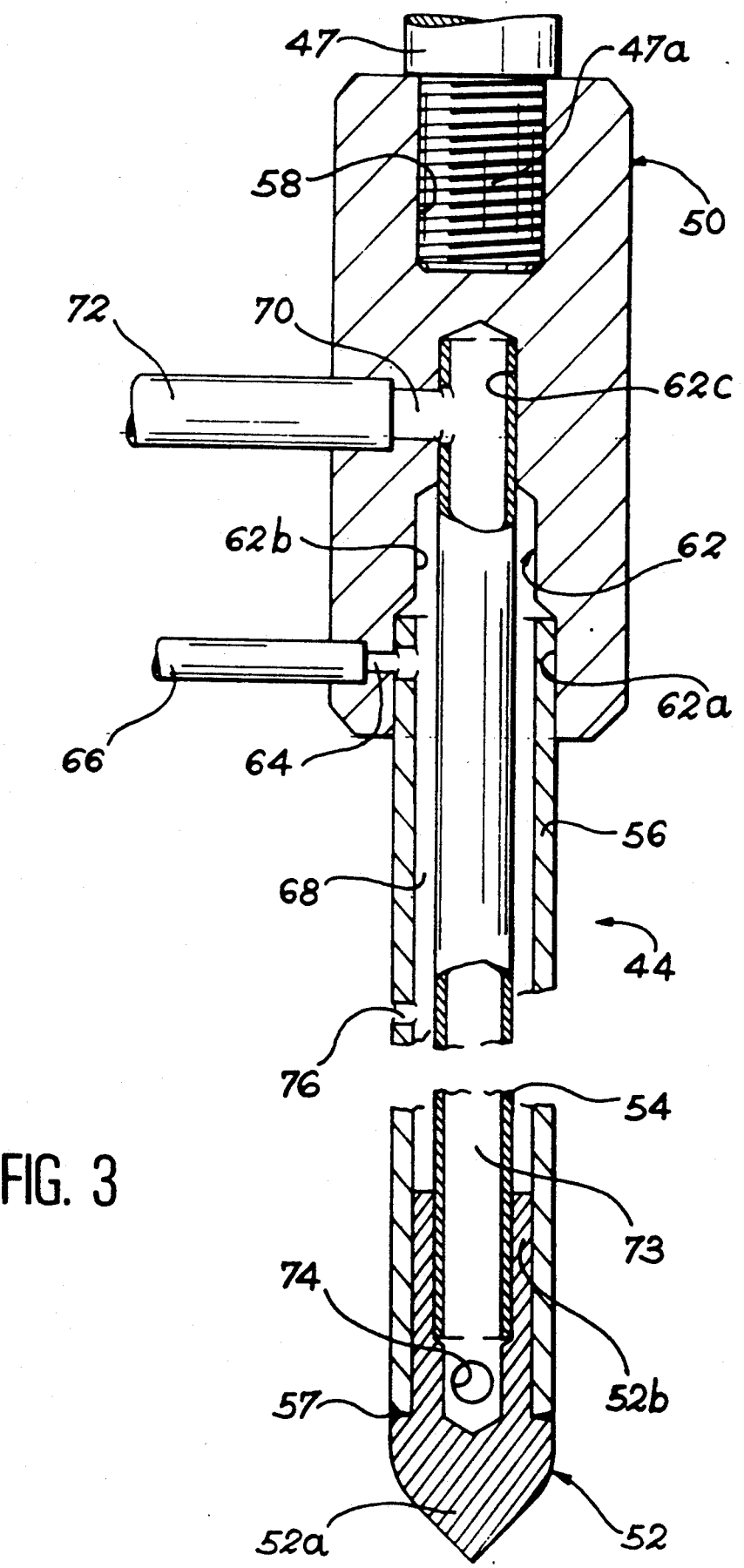
FIG. 3 A longitudinal sectional view on a larger scale of the double-walled needle equipping the flask emptying and rinsing station shown in FIG. 2.

As is illustrated in greater detail by FIG. 3, the double-walled needle 44 has a head 50, a point or tip 52 and two coaxial tubular walls respectively constituted by an inner tubular wall 54 and an outer tubular wall 56.

At its upper end, the head 50 has a taphole 58, by which the needle 44 is fixed to the threaded end 47a of the rod 47 of the needle holder jack 46. At its lower end, the head 50 has a staged bore 62 aligned with the taphole 58. This bore 62 has a relatively large diameter lower portion 62a in which is received the upper end of the outer tubular wall 56, a medium diameter intermediate portion 62b and a relatively small diameter upper portion 62c, in which is received the upper end of the inner tubular wall 54.

The head 50 has a first coupling connected by a passage 64 to the lower portion 62a or to the intermediate portion 62b of the staged bore 62. On said first coupling is mounted a tube 66 making it possible to inject a pressurized gas such as compressed air or a pressurized rinsing liquid such as water into an annular space 68 defined between the tubular walls 54, 56.

The head 50 also has a second coupling connected by a passage 70 to the upper part of the staged bore and on which is fitted a tube 72 making it possible to discharge the different fluids from the flasks by a central passage 73 formed in the inner tubular wall 54.

The tip 52 of the needle 44 forms at its lower end a perforating core 52a enabling the needle to pass through the plastics material wall of the flasks. The tip 52 also has a tubular upper portion 52b around which is fitted the outer tubular wall 56 and in which is received the inner tubular wall 54. The tip 52 is advantageously fixed to the end of the outer tubular wall 56 by means of an argon weld 57.

At least one opening 74 passes radially through the lower end of the outer tubular wall 56 and the upper tubular portion 52b of the tip 52, so as to issue below the lower end of the inner tubular wall 54.

FIG. 3 also shows that the outer tubular wall 56 is advantageously traversed, in its upper portion in the vicinity of the head 50, by at least one opening 76 linking the annular passage 68 with the exterior.

The introduction tube 66 is connected at its end opposite to the needle 44 to a pressurized gas circuit, such as compressed air at approximately 2 bars by means of a first, not shown electrovalve and to a pressurized rinsing liquid circuit such as water at approximately 3 bars via a second not shown electrovalve. The discharge tube 72 is connected to an effluent discharge circuit.

The automated operation of the flask emptying and rinsing apparatus described hereinbefore is advantageously controlled by a programmable automaton, such as the SIEMENS SR501-U automaton, on the basis of information supplied by different sensors, such as optical sensors and in accordance with known procedures.

The emptying and rinsing apparatus operation will now be described with reference to FIGS. 1 and 2.

Figure 2:
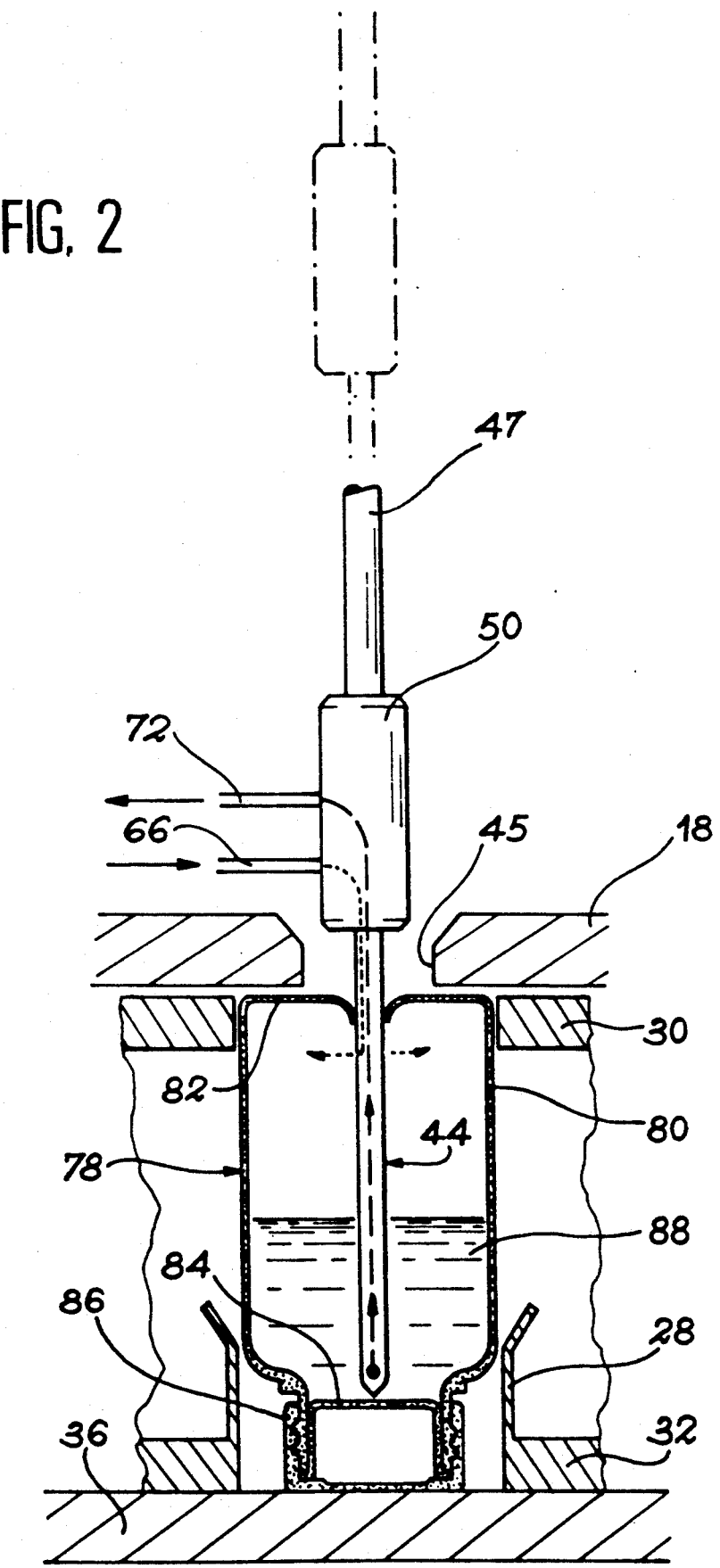
FIG. 2 A larger scale part sectional view showing the flask emptying and rinsing station in the apparatus of FIG. 1.

FIG. 2 shows on a larger scale one of the flasks 78, whose emptying and rinsing can be carried out with the aid of the apparatus according to the invention. This flask 78 has a body 80 having a circular section and in particular having a flat bottom 82 and which is made from a material which can be perforated by the tip or point of the needle 44, such as polyethylene. The mouth of the body 80 of the flask 78 is internally sealed by a cover 84 and externally sealed by a screw stopper 86. Each of the flasks is filled with a solution 88 which must be emptied and, in the embodiment described requires the rinsing of the flask before the latter is discharged into the drum.

As is diagrammatically illustrated by FIG. 1, the flasks to be emptied and rinsed are e.g. stacked in fours in the represented embodiment in each of the vertical tubular columns 16 of the rotary basket 10. More specifically, the flasks 78 are inverted before being placed in the columns 16, in such a way that their bottoms 82 are turned upwards.

When all the columns 16 are filled with flasks 78, the operation of emptying and rinsing them can commence. This operation, which is performed in a completely automatic manner, makes it possible to treat on average 60 flasks every hour without any handling operation having to be carried out in order to ensure the definitive conditioning of the flasks in the drums.

As soon as the apparatus is actuated, the basket 10 is rotated about the axis by a motor assembly 22. This rotation continues until one of the vertical tubular columns 16 arrives above the circular opening 24. The flasks 78 located in this said column then drop by gravity, in such as way that the lower flask is received in one of the receptacles 28 of the drum 26. This drop is detected by an optical fibre sensor 90 positioned level with the panel 18 and which automatically stops the motor assembly 22.

The drum 26 is then rotated by the motor assembly 40 until the flask 78 arrives to the right of the flask emptying and rinsing station. When the drum is in this position, detected by a not shown electrical sensor, another flask 78 drops by gravity into the receptacle 28, which is then located below the circular opening 24.

An emptying and rinsing cycle for the flask 78 located to the right of the emptying and rinsing station is then initiated. This cycle will now be described in greater detail relative to FIG. 2. At the start of the said cycle, the needle holder jack 46 is automatically operated in the sense of the fall of the double-walled needle 44. During this descent, the tip 52 of the needle perforates the flask bottom 82 and the needle passes into the flask until it arrives in the vicinity of the cover 84, in the lower emptying position illustrated in FIG. 2. This lower position is detected by a not shown magnetic sensor. The openings 76 are then located within the flask 78 slightly below the bottom 82 and above the solution 88.

The emptying of the solution 88 contained in the flask is then carried out by injecting compressed air (approximately 2 bars) above said solution through the tube 66, the annular passage 68 and the openings 76. The compressed air expels the solution 88 through the opening 74, the central passage 73 and the tube 72.

In the embodiment described, the flask 78 is then rinsed by injecting rinsing water through the tube 66, the annular passage 68 and the openings 76. The pressurized water (approximately 3 bars) is atomized within the flask, which optimizes the running down the walls and consequently the efficiency of rinsing.

The rinsing water is then expelled from the flask by a second compressed air injection carried out under the same conditions as the injection used for emptying the flask, but for a longer period.

When the pressure within the flask has returned to atmospheric pressure, which eliminates splashing during the exit of the needle 44, the latter is brought into its upper waiting position illustrated in FIG. 1 by the jack 46. As soon as a not shown magnetic contact detects the return of the needle 44 to said upper position, the motor assembly 40 is again actuated in order to bring the emptied and rinsed flask to the right of the discharge station and bring the following flask to the right of the emptying and rinsing station. The emptied and rinsed flask is then automatically discharged by gravity into the tubular collar 48 and a new emptying and rinsing cycle is initiated on the flowing flask. In this position, a third flask contained in the vertical tubular column 16, which is located above the circular opening 24 drops into the receptacle 28 placed below the said opening.

As soon as the optical sensor 90 level with the circular opening 24 detects that the column 16 located above said opening is empty, the motor assembly 22 is automatically actuated in order to bring another column 16 above said circular opening.

The cycle continues in this way until all the vertical tubular columns 16 are empty. The apparatus then stops automatically due to information supplied by a not shown electrical sensor responsible for counting the tubular columns 16.

Obviously, the invention is not limited to the embodiment described in exemplified manner hereinbefore and in fact covers all variants thereof.

Thus, the basket 10 and the drum 26, which constitute particular means for automatically passing the flasks to be emptied and rinsed in front of the double-walled needle by means of which said operations are performed, can in certain cases be eliminated, modified or replaced by equivalent means, such as a stepwise conveyor. Moreover, when the nature of the liquid contained in the flask to be emptied allows it, the rinsing operation can be eliminated.

We claim:

1. Apparatus for emptying flasks containing a liquid and comprising at least one perforatable partition, characterized in that it comprises a needle (44) having two coaxial walls, which can be inserted in the flask through the perforatable partition, the coaxial walls (54,56) of the needle defining a central passage (73) and an annular passage (68);

means (66) for injecting a pressurized gas into the needle by one of the said passages, so as to empty the liquid through the other passage (73);

a rotary drum (26) able to rotate about a vertical axis and having at least three cavities (28), each of which is able to receive an inverted flask;

means (40) for rotating the drum, so as to successively pass each cavity in front of a loading station, an emptying station having means (46) for moving said needle (44) between an upper waiting position and a lower discharge position, a discharge station;

a rotary basket (10) able to rotate about a vertical axis parallel to the drum axis, said basket incorporating vertical tubular columns (16) in which can be placed several inverted flasks;

a fixed horizontal panel (18) placed below the basket and on which rests the said flasks; and means (22) for rotating the basket, so as to successively bring each tubular column (16) above an opening (24) formed in the panel, said opening defining the loading station of the rotary drum (26) placed below the said panel.

2. Apparatus according to claim 1, characterized in that it also comprises, for rinsing the emptied flasks, means (66) for injecting a pressurized rinsing liquid through the first passage (68).

3. Apparatus according to claim 1, characterized in that the first passage is the annular passage (68) defined between the coaxial walls of the needle.

* * * * *